United States Patent [19]

Lin

[11] Patent Number: 5,607,428
[45] Date of Patent: Mar. 4, 1997

[54] ORTHOPEDIC FIXATION DEVICE HAVING A DOUBLE-THREADED SCREW

[76] Inventor: Kwan C. Lin, 45 Duncan St., Staten Island, N.Y. 10304

[21] Appl. No.: 431,758

[22] Filed: May 1, 1995

[51] Int. Cl.⁶ .................................................. A61B 17/56
[52] U.S. Cl. ................................................ 606/69; 606/73
[58] Field of Search .................................. 606/60, 61, 65, 606/69, 70, 71, 72, 73; 411/182, 366, 437

[56] References Cited

U.S. PATENT DOCUMENTS

| | | | |
|---|---|---|---|
| 4,388,921 | 6/1983 | Sutter et al. | 128/92 B |
| 4,978,265 | 12/1990 | De Wan | 411/60 |
| 5,085,660 | 2/1992 | Lin . | |
| 5,147,363 | 9/1992 | Harle | 606/73 |
| 5,257,994 | 11/1993 | Lin . | |
| 5,306,275 | 4/1994 | Bryan | 606/61 |
| 5,330,474 | 7/1994 | Lin . | |

FOREIGN PATENT DOCUMENTS 2254298  12/1973  France ..................... 606/73

Primary Examiner—Michael Powell Buiz
Assistant Examiner—David O. Reip
Attorney, Agent, or Firm—Bacon & Thomas

[57] ABSTRACT

An orthopedic fixation device includes a fixation plate having at least one through hole in which a direction adjusting ring is held securely. The direction adjusting ring is provided with an inner threaded hole engageable with a second threaded portion of a double-threaded bone screw. Located at a lower portion of the double-threaded bone screw is a first threaded portion which is fastened onto a bone or vertebra. Located at the top end of the double-threaded bone screw is a head for urging and spreading a plurality of arresting edges located at the upper side of the direction adjusting ring so as to cause the direction adjusting ring to be retained securely in the round through hole of the fixation plate. The axis of the threaded hole of the direction adjusting ring forms with the axis of an outer ring body of the direction adjusting ring an angle ranging between 3 and 15 degrees.

3 Claims, 2 Drawing Sheets

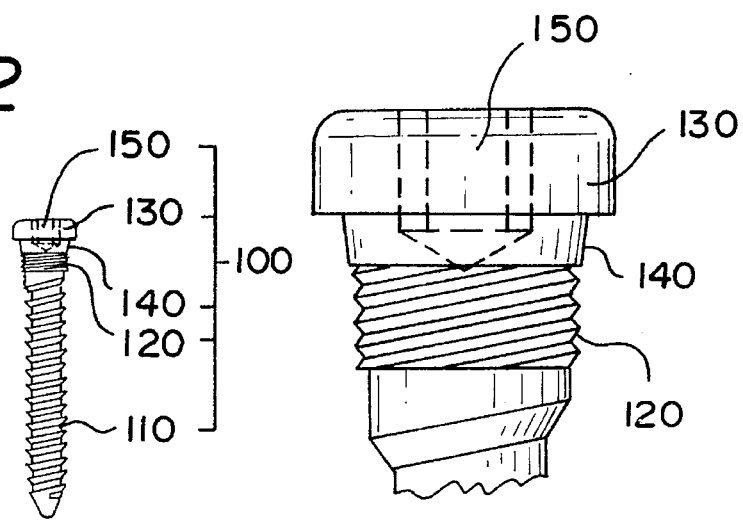
FIG. 2
FIG. 2A
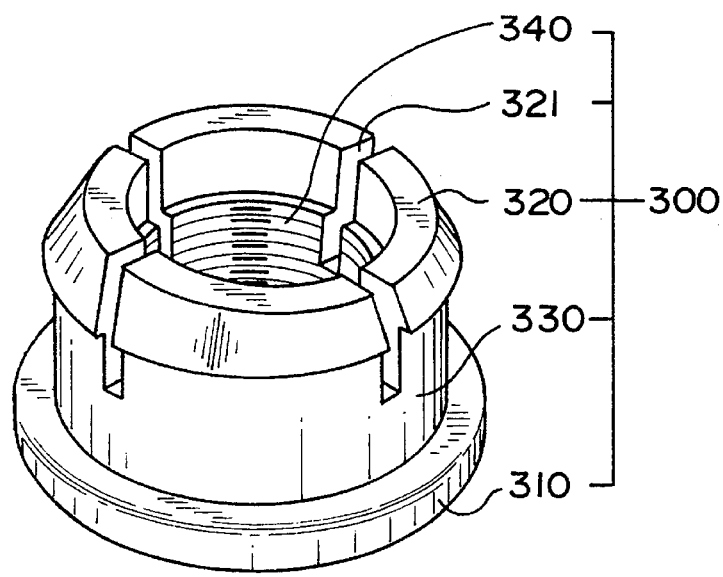
FIG. 3
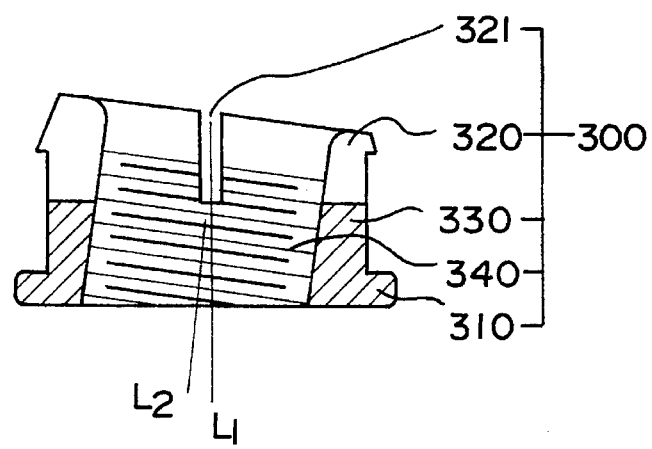
FIG. 4

ORTHOPEDIC FIXATION DEVICE HAVING A DOUBLE-THREADED SCREW

FIELD OF THE INVENTION

The present invention relates generally to an orthopedic fixation device, and more particularly to an orthopedic fixation device which is provided with a double-threaded bone screw.

BACKGROUND OF THE INVENTION

As disclosed by this inventor of the present invention in the U.S. Pat. No. 5,085,660, a vertebral fixation system comprises a double-threaded bone screw having a first threaded portion fro fastening onto a bone or vertebra, and a second threaded portion engageable with a fixation plate. The second threaded portion and the fixation plate are fastened at a right angle at which the first threaded portion is fastened onto a bone or vertebra. As a result, the angle at which the first threaded portion is fastened onto a bone or vertebra can not be changed in accordance with the surgical requirement when the fixation plate is chosen. Furthermore, the fixation plate is more rigid than the bone or vertebra onto which the double-threaded bone screw is fastened, thereby forcing the first threaded portion to fasten onto the bone or vertebra according to the advancing angle at which the second threaded portion is engaged with the fixation plate, if the angle at which the first threaded portion is fastened onto a bone or vertebra deviates from the advancing angle of the second threaded portion in the fixation plate. As a result, the threads formed by the first threaded portion in the bone or vertebra are vulnerable to damage and the first threaded portion of the double-threaded bone screw is therefore unable to hold the bone or vertebra securely.

SUMMARY OF THE INVENTION

It is therefore the primary objective of the present invention to provide an orthopedic fixation device with a direction adjusting ring and a double-threaded bone screw.

It is another objective of the present invention to provide an orthopedic fixation device comprising a double-threaded bone screw, a fixation plate or block, and a direction adjusting ring.

In keeping with the principle of the present invention, the foregoing objectives of the present invention are attained by an orthopedic fixation device comprising the component parts which are described hereinafter.

A fixation plate or block is provided with one or more round through holes.

A direction adjusting ring is provided on the inner side thereof with a threaded hole, and at the top thereof with a plurality of arresting edges, and a slit formed between any two of said a plurality of arresting edges, and further at the bottom thereof with a stopping edge. A round groove is formed by the arresting edge and the stopping edge which is capable of being retained in the through hole of the fixation plate or block.

A double-threaded bone screw comprises a threaded portion, a head, and a second threaded portion located between the first threaded portion and the head. The first threaded portion is intended to fasten onto a bone or vertebra. The threaded hole of the direction adjusting ring is engageable with the second threaded portion. The head of the double-threaded bone screw is used to urge the arresting edges of the direction adjusting ring so as to cause the direction adjusting ring to be retained securely in the round through hole of the fixation plate or block.

The direction adjusting ring of the fixation device of the present invention is characterized in that the axial direction of the threaded hole of the direction adjusting ring and the axial direction of the outer ring body form an angle ranging between 3 and 15 degrees.

The double-threaded bone screw of the present invention is similar in construction to any prior art double-threaded bone screw, such as the bone screw disclosed by this inventor of the present invention in U.S. Pat. No. 5,085,660. The first threaded portion of the double-threaded bone screw of the present invention is substantially corresponding in pitch to the second threaded portion of the double-threaded bone screw of the present invention. However, the second threaded portion comprises 2–4 starts, each of which is similar in pitch to one another and to the first threaded portion. It is suggested that a slanted body is provided between the second threaded portion and the head of the double-threaded bone screw so as to enable the double-threaded bone screw to urge the arresting edges of the direction adjusting ring when the direction adjusting ring is fastened by the double-threaded bone screw.

The fixation plate or block of the present invention is similar in construction to the prior art fixation plate which is disclosed by this inventor of the present invention in U.S. Pat. No. 5,085,660. The fixation plate or block of the present invention may be also similar in construction to the prior art lateral fixation block disclosed in U.S. Pat. Nos. 5,330,474 and 5,257,994. The fixation plate or block of the present invention has one or more round through holes, which may be modified in other forms to cooperate with other fixation systems.

The round groove of the direction adjusting ring of the present invention has an outer diameter equal to or slightly smaller than the inner diameter of the round through hole of the fixation plate or block. As a result, there is a considerable buffering gap to facilitate the insertion of the direction adjusting ring into the round through hole of the fixation plate or block. The arresting edges and the stopping edge of the direction adjusting ring have respectively an outer diameter which is slightly greater than the inner diameter of the round through hole of the fixation plate or block, so as to ensure that the ring body between the arresting edges and the stopping edge of the direction adjusting ring are held securely in the round through hole of the fixation plate or block. The arresting edges of the direction adjusting ring can be forced into the round through hole from the underside of the fixation plate or block by the contraction of the slits. As the threads of the threaded hole of the direction adjusting ring are urged intensively by the second threaded portion of the double-threaded bone screw, the arresting edges of the direction adjusting ring is pushed by the head of the double-threaded bone screw so that the direction adjusting ring is retained securely in the round through hole of the fixation plate or block. In the meantime, the first threaded portion of the double-threaded bone screw is fastened onto a bone or vertebra while the second threaded portion of the double-threaded bone screw is engaged with the threaded hole of the direction adjusting ring.

It was mentioned previously that a minute buffering gap exists between the direction adjusting ring and the round through hole of the fixation plate or block. When the double-threaded bone screw is put through the threaded hole of the direction adjusting ring such that the first threaded portion of the double-threaded bone screw is fastened onto a bone or vertebra, and that the second threaded portion of the double-threaded bone screw has begun to engage the threaded hole of the direction adjusting ring, an angle θ1 is formed by the double-threaded bone screw and the fixation plate or block. If the angle θ1 is different from the angle θ2 which is formed by the axis of the threaded hole of the direction adjusting ring and the fixation plate or block, the double-threaded bone screw must be further advanced. The further advancement of the double-threaded bone screw can bring about the rotation of the direction adjusting ring so that the angles θ1 and θ2 are equal to each other and that the direction adjusting ring is retained securely in the round through hole of the fixation plate or block. Thereafter, as the double-threaded bone screw is further advanced, the first threaded portion of the double-threaded bone screw will be further fastened onto the bone or vertebra. In the meantime, the second threaded portion of the double-threaded bone screw is caused to advance in the threaded hole of the direction adjusting ring until such time when the direction adjusting ring is held securely in the round through hole of the fixation plate or block. The slanted body of the direction adjusting ring is intended to facilitate the spreading of the arresting edges of the direction adjusting ring so as to attain an intimate and secure engagement of the direction adjusting ring with the round through hole of the fixation plate or block.

The axial direction of the threaded hole of the direction adjusting ring and the axial direction of the outer ring body of the direction adjusting ring form an angle ranging between 3 and 15 degrees.

BRIEF DESCRIPTION OF THE DRAWINGS

FIG. 2 and FIG. 2A show, respectively, the preferred embodiment and an enlarged schematic view of the head and the slanted body of the preferred embodiment as shown in FIG. 1.

FIG. 3 shows an enlarged perspective view of the direction adjusting ring of the preferred embodiment as shown in FIG. 1.

FIG. 4 shows an enlarged sectional view of the direction adjusting ring of the preferred embodiment as shown in FIG. 1.

DETAILED DESCRIPTION OF THE EMBODIMENTS

Figure 1A:
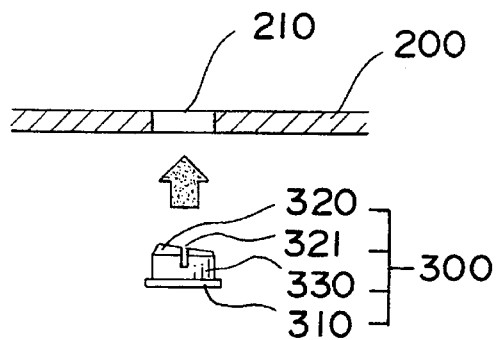
FIGS. 1a–1d are schematic views illustrating the combination process of a preferred embodiment of the present invention.
Figure 1B:
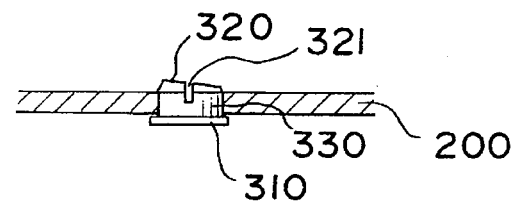
Figure 1C:
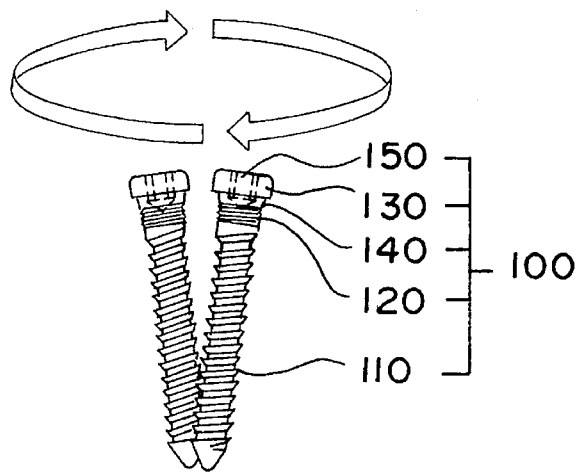
Figure 1D:
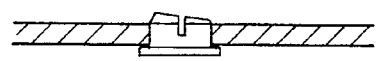
Figure 1D:
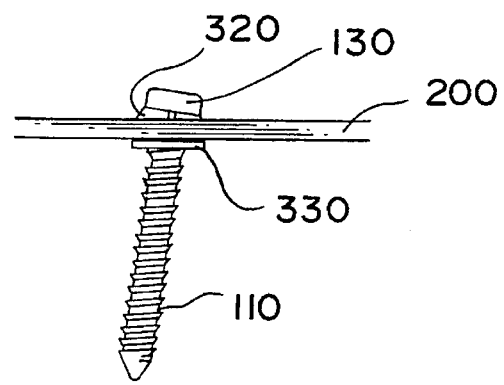

As shown in FIGS. 1a–1d, the fixation device embodied in the present invention comprises a double-threaded bone screw 100, a fixation plate 200, and a direction adjusting ring 300. The double-threaded bone screw 100 is provided with a first threaded portion 110, a second threaded portion 120, a head 130, a slanted body 140, and a tool hole 150. The direction in which the head 130 is turned is indicated by two arrows as shown in FIG. 1c. The fixation plate 200 is provided with a round through hole 210. The direction adjusting ring 300 is provided with a lower stopping edge 310, upper arresting edges 320, and a round groove 330. The upper arresting edges 320 is provided with a slit 321 between any two of the upper arresting edges 320. The direction adjusting ring 300 is forced into the round through hole 210 of the fixation plate 200 from the underside of the fixation plate 200, as indicated by an arrow in FIG. 1a. As shown in FIG. 1d, the threaded portion 110 of the double-threaded bone screw 100 is fastened onto a bone or vertebra (not shown in the drawing) while the second threaded portion 120 is threaded into the threaded hole 340 of the direction adjusting ring 300.

For the purpose of illustrating the unique construction of the fixation device of the present invention, the upper portion of the double-threaded bone screw 100, as shown in FIG. 2, is enlarged five times, as shown in FIG. 2A. The slanted body 140 is shown to have an inclined surface.

As shown in FIG. 3, the direction adjusting ring 300 is additionally provided with a threaded hole 340.

As shown in FIG. 4, the direction adjusting ring 300 of the present invention has an outer ring body axis L1 and an inner threaded hole axis L2. The axes L1 and L2 form an angle of 7 degrees according to the preferred embodiment of the present invention.

What is claimed is:

1. An orthopedic fixation device comprising:
   a fixation plate having at least one round through holes;
   a direction adjusting ring having an inner threaded hole, a plurality of arresting edges located at an upper side thereof, a stopping edge located at a lower side thereof, and a slit formed between any two arresting edges of said a plurality of arresting edges; and
   a double-threaded bone screw provided at a lower end thereof with a first threaded portion for fastening onto a bone or vertebra, said double-threaded bone screw further provided at an upper end thereof with a head for urging and spreading said a plurality of arresting edges so as to cause said direction adjusting ring to be retained securely in said round through hole of said fixation plate, said double-threaded bone screw still further provided with a second threaded portion located between said first threaded portion and said head and engageable with said inner threaded hole of said direction adjusting ring;
   wherein said inner threaded hole of said direction adjusting ring has an axis which forms with an axis of an outer ring body of said direction adjusting ring an angle ranging between 3 and 15 degrees.

2. The orthopedic fixation device as defined in claim 1, wherein said double-threaded bone screw is provided with a slanted body located between said second threaded portion and said head.

3. The orthopedic fixation device as defined in claim 1, wherein the threads of said second threaded portion of said double-threaded bone screw have 2–4 starts, each of which is similar in pitch to the threads of said first threaded portion.

* * * * *